United States Patent [19]

Masini et al.

[11] Patent Number: 4,978,435

[45] Date of Patent: Dec. 18, 1990

[54] FREE CHLORINE REMOVAL PROCESS

[75] Inventors: Jean-Jacques Masini, Chaponost; Bertrand Collier, Saint Genis Laval, both of France

[73] Assignee: Atochem, Puteaux, France

[21] Appl. No.: 235,906

[22] Filed: Aug. 24, 1988

[30] Foreign Application Priority Data

Aug. 27, 1987 [FR] France ..................... 87 11990

[51] Int. Cl.[5] ..................... B01J 19/08; C07C 17/10; C07C 17/38

[52] U.S. Cl. ..................... 204/157.94; 204/157.95; 204/157.96; 204/158.12; 570/253; 570/255; 570/261; 570/262

[58] Field of Search ..................... 204/157.94, 157.95, 204/157.96, 157.98, 158.1, 158.12; 570/253, 255, 261, 262

[56] References Cited

U.S. PATENT DOCUMENTS

| | | | |
|---|---|---|---|
| 2,606,867 | 8/1952 | Pianfetti | 204/158.12 |
| 2,899,370 | 8/1959 | Rosenberg | 204/158.12 |
| 2,997,508 | 8/1961 | Stretton | 204/158.12 |
| 3,259,561 | 7/1966 | Sievers | 204/158.12 |
| 3,296,108 | 1/1967 | Hutson | 204/158.12 |
| 3,344,197 | 9/1967 | Reiche | 570/253 |
| 3,402,114 | 9/1968 | Hutson | 204/158.12 |
| 3,474,018 | 10/1969 | Goeb | 204/157.94 |
| 3,494,844 | 2/1970 | Holiday | 204/158.12 |
| 3,506,553 | 4/1970 | Mottern | 570/255 |
| 3,528,900 | 9/1970 | Rosenberg | 204/158.12 |
| 3,745,103 | 7/1973 | Richtzenhain | 204/157.94 |
| 3,748,243 | 7/1973 | Christialns | 204/157.94 |
| 4,689,130 | 8/1987 | Masini | 204/157.94 |
| 4,765,876 | 8/1980 | Masini | 204/157.95 |

FOREIGN PATENT DOCUMENTS

| | | |
|---|---|---|
| 890730 | 2/1944 | France . |
| 1181751 | 6/1959 | France . |
| 1362507 | 4/1964 | France . |

*Primary Examiner*—John F. Niebling
*Assistant Examiner*—Ben C. Hsing
*Attorney, Agent, or Firm*—Burns, Doane, Swecker & Mathis

[57] ABSTRACT

Free chlorine values are removed by radical chlorination from uncombined admixtures thereof, notably admixtures of free chlorine and at least one halogenated organic compound that is not completely chlorö-substituted.

9 Claims, 1 Drawing Sheet

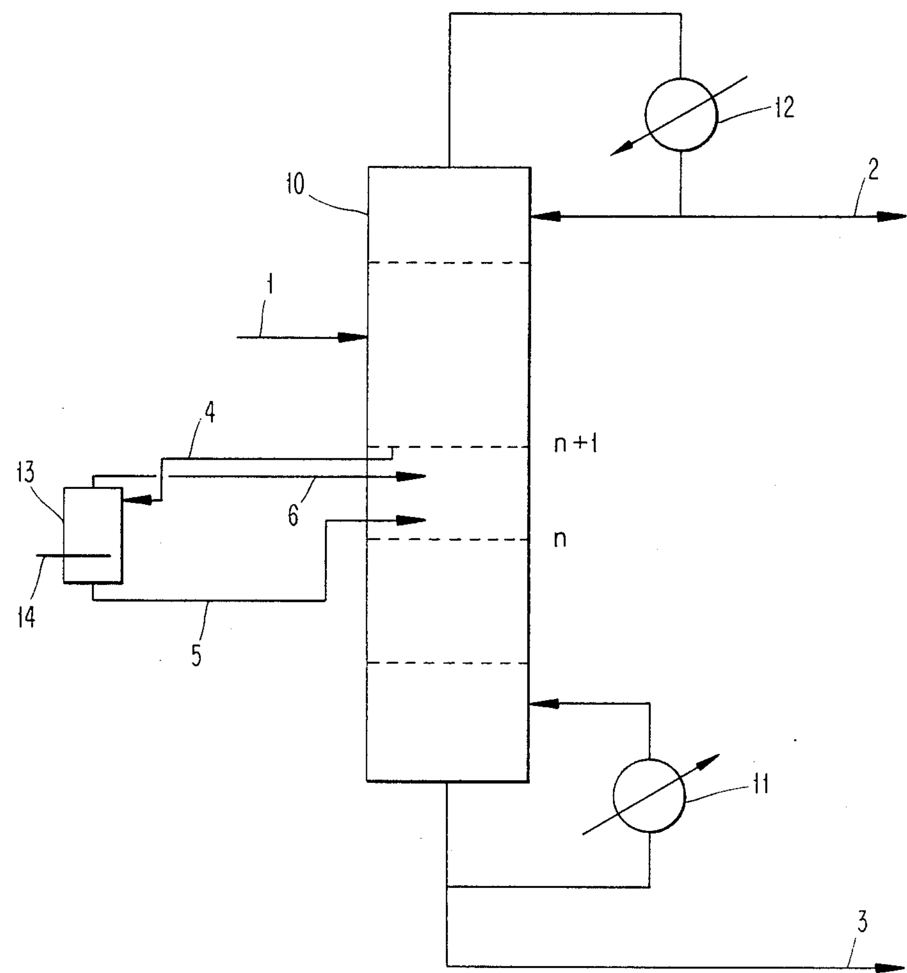
12
10
2
1
4
n+1
13
6
n
14
5
11
3

FREE CHLORINE REMOVAL PROCESS

BACKGROUND OF THE INVENTION

1. Field of the Invention:

The present invention relates to the removal of free chlorine present in certain admixtures thereof, and, more especially, from admixtures of free chlorine and at least one haloorganic compound that is not completely chlorosubstituted.

2. Description of the Prior Art:

Mixtures of compounds containing dissolved free chlorine and organic compounds "unsaturated" in respect of chlorine atoms are frequently encountered in the chemical industry, for example during the synthesis of trichloroethanes. U.S. Pat. No. 3,474,018 describes a process for the synthesis of 1,1,1-trichloroethane; one of the stages of the process is a separation of ethyl chloride from a mixture of chloroethanes containing dissolved chlorine. Distillation of such mixtures containing chlorine can give rise to corrosion (see Kirk Othmer, 3rd edition, vol. 1, pages 835 et seq). U.S. Pat. No. 3,344,197 also refers to the corrosion risks inherent in the presence of chlorine.

SUMMARY OF THE INVENTION

Accordingly, a major object of the present invention is the provision of an improved process for the removal of even trace amounts of free chlorine values from uncombined admixtures thereof without having to resort to distillation procedures which are all the more complex in attempting to rid a system of trace amounts of unwanted species.

Briefly, the present invention features a process for removing the free chlorine present in a mixture comprising at least one halogenated organic compound which is incompletely chlorine substituted (chloro-unsaturated compound), and wherein such mixture is subjected to a radical chlorination.

BRIEF DESCRIPTION OF THE DRAWINGS

The Figure of Drawing is a schematic/diagrammatic representation of the process/apparatus according to the present invention.

DETAILED DESCRIPTION OF THE PREFERRED EMBODIMENTS OF THE INVENTION

More particularly according to the present invention, all such mixtures comprising free chlorine values are comprehended hereby, particularly those consisting essentially of organic compounds.

The invention is especially applicable to mixtures containing only free chlorine and a haloorganic compound not completely substituted by chloro substituents ("chloro-unsaturated compound"), this mixture containing a solvent, if appropriate.

By "chloro-unsaturated compound" is intended any halogenated compound which still has at least one hydrogen atom capable of being substituted by chlorine.

The invention is also applicable to mixtures containing any proportion of chlorine, but it is primarily useful in the case of mixtures containing minor amounts of chlorine. When the mixture contains much chlorine, that is to say, more then 5 or 10% by weight, the mixture can be treated by flash and/or fractional evaporations/condensations, or partial distillations to remove the larger proportion of the chlorine. The invention is preferably applicable to mixtures containing less than 5% and in most cases less than 0.1% of chlorine (by weight).

The mixture must contain one or more organic compounds which are not completely substituted by chlorine substituents, in sufficient quantity to consume the free chlorine. The radical chlorination is a reaction known per se.

This process may be carried out employing chemical initiation or photochemical initiation. In the case of chemical initiation, the known initiators for chlorination reactions can be employed.

Exemplary thereof are diazo compounds such as 2,2'-azobisisobutyronitrile or 2,2'-azobis-2,3-dimethylvaleronitrile, or peroxide compounds such as lauroyl peroxide or benzoyl peroxide. As a general rule, the compounds may be employed as such or in the form of a solution, especially in solution in a chloroalkane.

It is possible according to the invention to obtain a degree of chlorine conversion of more than 99% and more precisely more than 99.5% with a quantity of initiator which generally ranges from $10^{-2}$ to $2\times10^{-6}$ and preferably from $5\times10^{-3}$ to $10^{-5}$ mole of initiator per mole of chlorine, in the case of the initiators which have a dissociation constant, in toluene, of from $5\times10^{-7}$ to $5\times10^{-4}$ $s^{-1}$ and preferably from $10^{-6}$ to $2\times10^{-4}$ $s^{-1}$.

By way of example, and assuming a photochemical initiator, a degree of chlorine conversion of more than 99% and more precisely of more than 99.5% may be obtained for a luminance of from 0.5 to 2 $W/cm^2$ (total electrical power of the emitter, related to the external surface area of the enclosure corresponding to the length of the electrical arc of the light source) and an electricity consumption corresponding to a photoelectric emission of from 0.1 to 100 Wh/mole and more particularly from 0.5 to 70 Wh/mole of chlorine employed.

Any vessel whatsoever may be employed to carry out the reaction: a storage tank, a length of piping, a tray of a distillation column, the reboiler of a column, etc. It is sufficient to merely distribute the initiator or the radiation well throughout the mixture and to adopt a residence time to consume the chlorine in the proportions indicated above.

The operation may be carried out in gaseous or liquid phase or with a partially liquid mixture. Although the operation may be carried out over a wide temperature range, it is preferable to conduct the reaction above 20° C. and preferably at a temperature of from 40° C. to 100° C. The kinetics of the disappearance of chlorine increase with the temperature. The residence time required to consume all of the chlorine generally ranges from a few seconds to one hour, in the case of temperatures above 50° C. Although the operation can be carried out over a wide range of pressures, it is generally carried out at a pressure of from 1 to 50 bars and preferably from 7 to 13 bars.

The invention is particularly applicable to mixtures of chloroalkanes. In the synthesis of chloroalkanes, chlorine is reacted with alkanes or chloroalkanes which still have available sites capable of being substituted by chlorine. The alkanes and the chloroalkanes may be in gaseous or liquid phase, with or without solvent. Upon completion of the reaction, alkanes and/or chloroalkanes which are substituted to various degrees, hydrochloric acid, unreacted chlorine and, if appropriate, solvent are obtained. The chloroalkanes must be separated, either to be obtained separately and pure, or to be recycled into another phase of the process. Processes of this type are described, for example, in European Pat. application No. EP 0,128,818 and in British Pat. application No. GB 2,158,067.

The liquid, gaseous, or liquid and gaseous products exiting the reactor(s), namely, mixtures of chloroalkanes, HCl and chlorine, are treated with an array of distillation columns which permit successive separation of HCl from the chloroalkanes and then of each of the chloroalkanes. Chlorine concentrates in the stripping section of the column for separating HCl from the chloroalkanes.

The invention is applicable to the mixture present in the stripping section of this column. The chemical initiator may be injected into the column, or UV emitters may be arranged in the column.

Advantageously, (i) the liquid mixture taken from a tray of the column or, in the case of a packed column, from a distribution tray is drawn off, (ii) a radical chlorination of this mixture is carried out, and then (iii) the mixture which has been purified in respect of chlorine is reinjected into the column.

A preferred embodiment of the process of the invention is shown in the attached Figure of Drawing.

A distillation column 10 equipped with a reboiler 11 and a reflux condenser 12 is charged via line 1 with a mixture of chloroalkanes, HCl and chlorine. The HCL is removed at outlet 2 and the chloroalkanes at outlet 3.

The chlorination reactor 13 is charged with liquid from a tray n+1 via a conduit 4 and then the liquid phase which may contain dissolved HCl exits the reactor 13 and returns to the column via the conduit 5 onto the tray n. A conduit 6 connects the vapor phase of the reactor 13 to the vapor phase of the column 10. The reactor 13 contains one or more UV emitters 14. When the UV emitter is actuated, the two streams 2 and 3 contain no chlorine, and the chlorine present in the stream 1 has therefore been consumed; when the UV emitter is not operated, the chlorine present in the stream 1 is transferred into the chloroalkane stream 3.

The present invention also features a process for the synthesis of chloroalkanes employing 2 reactors connected in series, wherein:

(a) chloroalkanes are synthesized by radical chlorination in the first reactor;

(b) the products obtained are treated to concentrate the unreacted chlorine; and (c) the resultant mixture, which contains chlorine and at least one chloroalkane unsaturated (incompletely chloro-substituted) in respect of substituted chlorine, is subjected to a radical chlorination in order to remove the chlorine present in such mixture.

The first of the reactors in series is not necessarily a single reactor, but is intended to connote a reaction unit, for example a set of 2 reactors in parallel, as described in European Pat. application No. 128,818, or a loop reactor, as in British Pat. No. GB 2,158,067. Reactants and chlorine are introduced into this first reactor. A mixture containing HCl, chloroalkanes and unreacted chlorine is obtained. The products can be separated by distillation; HCl, being the most volatile, is separated first, and the chloroalkanes are then separated, beginning with the most volatile such chloroalkanes which are also those least saturated or substituted with chlorine, and the saturated chloroalkanes are then withdrawn upon completion of the distillation. The chlorine accompanies the unsaturated chloroalkanes. As a result of the distillation, the chlorine present in the products exiting the stage (a) is concentrated. Depending on the product purities required, products containing free chlorine have to be distilled. In order to avoid difficult separations which could give rise to corrosion, as aforesaid, it has now unexpectedly been discovered how to remove the chlorine present in these mixtures containing a chloroalkane unsaturated in respect of chloro substituents.

In a preferred embodiment of the invention, the mixture of HCl, chlorine and chloroalkanes exiting the stage (a), partially gaseous if appropriate, is introduced into a conventional distillation column (stage b). The HCl is withdrawn at the head, the stage (c) is carried out in the stripping section, preferably at a height of a theoretical plate whose temperature ranges from 40° C. to 100° C., and the chloroalkanes exit at the base thereof.

The advantage of a process of this type is that a radical chlorination can be carried out in the stage (a) without the requirement for precise monitoring of the possible excess of chlorine. Another advantage is that the presence of chlorine is eliminated in the lower part of the separation column, where the temperature is at its maximum, and this limits possible corrosion problems. Another advantage is that the chlorine content in the lightest chloroalkane, which is obtained at the head of the following column, is limited. Another advantage is that the by-product HCl is separated immediately from the reaction products; this HCl exits at the head of the column and chlorine-free chloroalkanes are recovered from the base.

In order to further illustrate the present invention and the advantages thereof, the following specific example is given, it being understood that same is intended only as illustrative and in nowise limitative.

EXAMPLE

The apparatus was that illustrated in the Figure of Drawing. The column comprised 50 trays, the reactor 13 was arranged between trays 18 and 19 (numbered beginning at the base of the column) and assumed the shape of a vertical tube 0.2 m in diameter and 3.8 m in height, in which an UV emitter with a power of 10 kW was arranged.

The effective column pressure was 12 bars, the head temperature −25° C. and the base temperature 114° C.

The feedstream 1 had the following composition:

| | |
|---|---|
| HCl | 28% |
| $CH_3Cl$ | 8.5% |
| $CH_2Cl_2$ | 16.1% |
| $CHCl_3$ | 26.4% |
| $CCl_4$ | 21% |
| $Cl_2$ | 400 ppm |

The percentages are by weight, the throughput was 28,250 kg/h and the feed point was onto tray 35. It was determined that streams 2 and 3 no longer contained chlorine.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the removal of free chlorine values from an admixture of HCl, free chlorine and at least one chloro-unsaturated compound comprising introducing the admixture into a stripping zone from a distillation column for separating HCl from the admixture, radical chlorinating the admixture in the stripping zone, and returning the chlorine free admixture to the distillation column.

2. The process as defined by claim 1, said at least one chloro-unsaturated compound comprising a chloroalkane.

3. The process as defined by claim 2, said admixture comprising less than 5% by weight of free chlorine.

4. The process as defined by claim 3, said admixture comprising less than 0.1% by weight of free chlorine.

5. The process as defined in claim 2, said radical chlorinating being initiated by chemical or photochemical means.

6. The process as defined by claim 2, said admixture further comprising a solvent.

7. The process as defined by claim 1, said radical chlorinating being initiated by chemical or photochemical means.

8. The process as defined by claim 1, said admixture further comprising a solvent.

9. A process for the production of chloroalkanes, comprising (a) preparing a reaction product comprising chloroalkanes, HCl, and unreacted chlorine by radical chlorination in a first reaction zone, (b) concentrating unreacted chlorine in the reaction product so as to provide an admixture, and (c) radical chlorinating the admixture in a second reaction zone.

* * * * *